United States Patent [19]

Measells et al.

[11] Patent Number: 4,892,604
[45] Date of Patent: Jan. 9, 1990

[54] METHOD OF MAKING A STERILIZABLE MULTI-LAYER CONTAINER

[75] Inventors: Paul E. Measells, Palatine; William D. Johnston, Buffalo Grove; Peter C. Kwong, McHenry; Dean G. Laurin, Lake Zurich; Leonard F. Czuba, Lombard, all of Ill.

[73] Assignee: Baxter International Inc., Deerfield, Ill.

[21] Appl. No.: 143,295

[22] Filed: Jan. 7, 1988

Related U.S. Application Data

[63] Continuation of Ser. No. 59,132, Jun. 1, 1987, abandoned, which is a continuation of Ser. No. 827,847, Feb. 7, 1986, abandoned.

[51] Int. Cl.⁴ .................. B32B 31/26; B32B 31/28
[52] U.S. Cl. .................. 156/244.24; 156/272.2; 156/275.1; 156/290; 156/292; 156/308.4
[58] Field of Search .......... 604/403, 408, 266; 428/35, 515; 128/D 27; 156/84, 85, 244.13, 244.14, 244.17, 244.24, 229, 272.2, 273.3, 273.5, 273.7, 275.1, 290, 292, 308.2, 308.4, 309.6; 426/127, 113, 412; 264/248

[56] References Cited

U.S. PATENT DOCUMENTS

| | | |
|---|---|---|
| 2,855,517 | 10/1958 | Rainer et al. |
| 2,981,668 | 4/1961 | Brasch |
| 3,022,254 | 2/1962 | Jones et al. |
| 3,075,857 | 1/1963 | Fior et al. |
| 3,274,004 | 9/1966 | Curter et al. |
| 3,298,597 | 1/1967 | Bellamy, Jr. .......... 604/408 |
| 3,419,654 | 12/1968 | Chiba et al. |
| 3,486,196 | 12/1969 | Klenk et al. |
| 3,508,944 | 4/1970 | Henderson et al. |
| 3,595,735 | 7/1971 | Tyrrell |
| 3,639,502 | 2/1972 | Okazaki et al. |
| 3,673,055 | 6/1972 | Sheld |
| 3,700,751 | 10/1972 | Mueller et al. |
| 3,767,523 | 10/1973 | Schwarz |
| 3,832,270 | 8/1974 | Schirmer |
| 3,886,056 | 5/1975 | Kitamaru et al. |
| 3,932,692 | 1/1976 | Hirata et al. |
| 4,104,404 | 8/1978 | Bieler et al. |
| 4,107,380 | 8/1978 | Wiezman .......... 428/520 |
| 4,352,702 | 10/1982 | Bornstein .......... 156/244.17 |
| 4,453,940 | 6/1984 | Aoyagi et al. .......... 128/DIG. 24 |
| 4,482,585 | 11/1984 | Ohodaira et al. .......... 604/408 |
| 4,507,123 | 3/1985 | Yoshida .......... 604/408 |
| 4,516,977 | 5/1985 | Herbert .......... 604/408 |
| 4,528,220 | 7/1985 | Hwo .......... 604/408 |
| 4,561,110 | 12/1985 | Herbert .......... 604/408 |

FOREIGN PATENT DOCUMENTS

| | | |
|---|---|---|
| 0068271 | 1/1983 | European Pat. Off. |
| 0168755 | 1/1986 | European Pat. Off. .......... 604/408 |
| 3247294 | 7/1983 | Fed. Rep. of Germany |
| 8304946 | 7/1983 | Fed. Rep. of Germany |
| 35-8943 | 7/1960 | Japan |
| 39-19052 | 9/1964 | Japan |
| 44-27477 | 11/1969 | Japan |
| 48-19230 | 6/1973 | Japan |
| 49-114688 | 11/1974 | Japan |
| 11804 | 4/1976 | Japan |
| 79684 | 7/1976 | Japan |
| 111805 | 9/1976 | Japan |
| 0026492 | 3/1978 | Japan .......... 604/408 |
| 0004975 | 1/1979 | Japan .......... 428/515 |
| 54-64685 | 5/1979 | Japan |
| 55-72664 | 5/1980 | Japan |
| 0046750 | 4/1981 | Japan .......... 428/35 |
| 56-046750 | 4/1981 | Japan |
| 57-175365 | 4/1981 | Japan |
| 0116469 | 9/1981 | Japan .......... 604/408 |
| 0175365 | 10/1982 | Japan .......... 604/408 |
| 2149345 | 6/1985 | United Kingdom |

*Primary Examiner*—Merrell C. Cashion, Jr.
*Attorney, Agent, or Firm*—Paul C. Flattery; Rockwell, Amy L. H.; Charles R. Mattenson

[57] ABSTRACT

A sterilizable, plastic medical container has a body section formed of thin, multi layer film. The film has a first layer formed of cross-linkable plastic free or essentially free of extractable plasticizers, such as poly(ethylene vinyl acetate), and a second layer formed of a substantially non-cross-linkable plastic having a higher melting temperature than the first layer, such as high density polyethylene. The first layer is inwardly oriented in contact with the contents of the container. A port formed of the same plastic can be heat sealed to the body section. The container is irradiated to effect cross-linking, filled with fluid, and the port sealed. The fluid filled container can then be heat or steam sterilized.

9 Claims, 3 Drawing Sheets

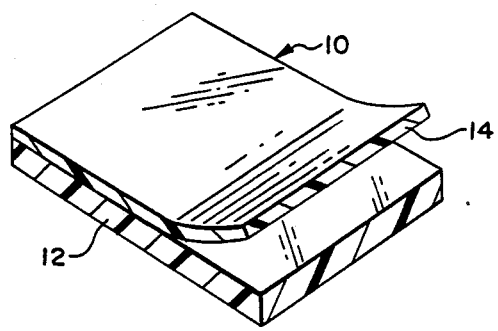
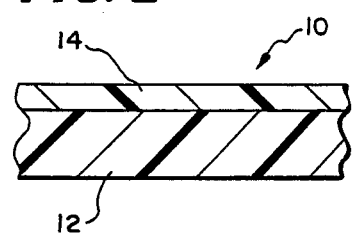
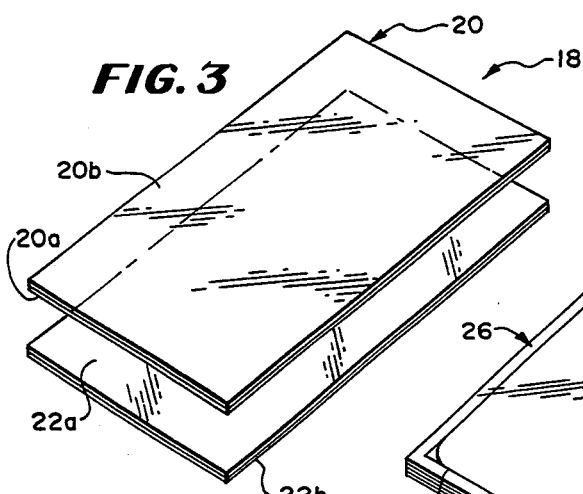
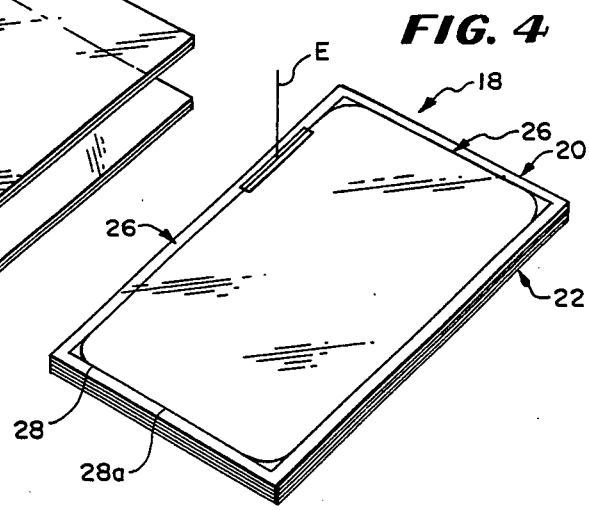
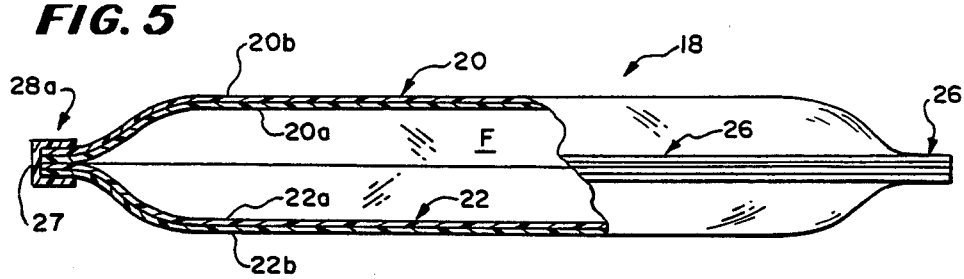

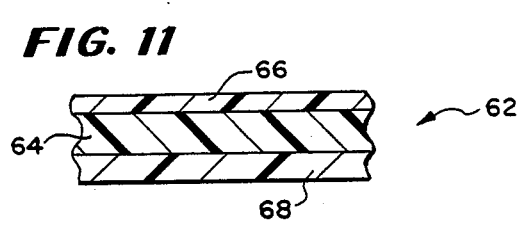
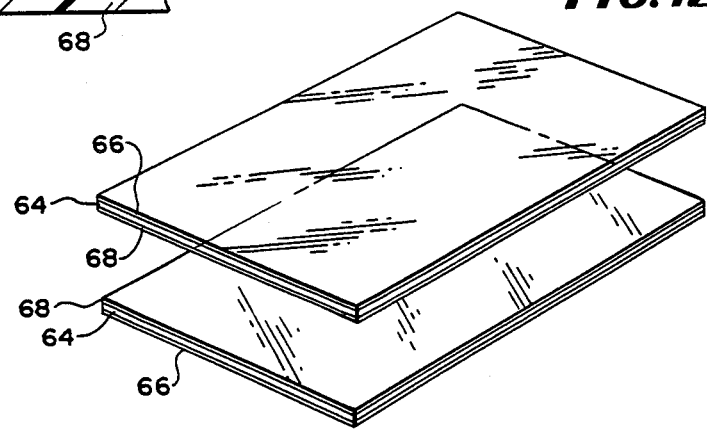
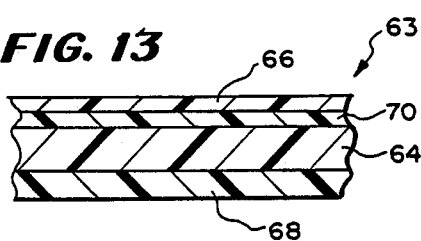
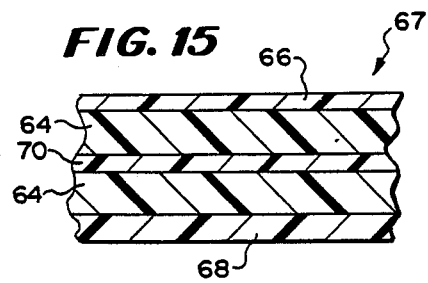
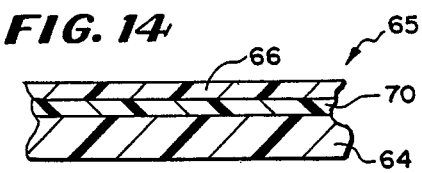
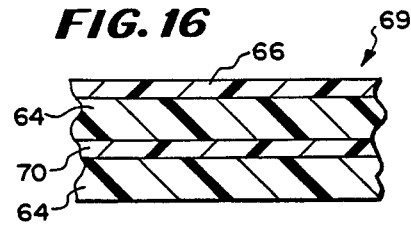

METHOD OF MAKING A STERILIZABLE MULTI-LAYER CONTAINER

This is a continuation of co-pending application Ser. No. 059,132 filed on June 1, 1987 which is a continuation of application Ser. No. 827,847 filed on Feb. 7, 1986 (both now abandoned).

FIELD OF THE INVENTION

The invention pertains to multi-layer plastic materials and containers made therefrom. More particularly, the invention pertains to sterilizable multi-layer plastic materials and containers suitable for use in the medical field.

BACKGROUND OF THE INVENTION

Various forms of multi-layer plastic films are well-known in the art. For example, Schirmer U.S. Pat. No. 3,832,270, entitled "Heat Shrinkable, Oriented Laminated Plastic Film", discloses a multi-layer package wrapping film. The film of the Schirmer patent is a multi-layer laminate structure with a layer of ethylene-vinyl acetate bonded to a layer of polyethylene. Prior to the lamination step, the layer of ethylene-vinyl acetate is irradiated to effect cross-linking.

Further, Nakamura et al U.S. Pat. No. 4,465,487, entitled "Container for Medical Use", discloses a plastic container formed of ethylene-vinyl acetate. The collapsible container is formed of a single layer sheet material. This material has a preferred thickness in a range of 0.010–0.015 inch. The container is first heat sealed at its edges to provide fluid resistant seals. Then, the container is irradiated to provide desired cross-linking in the material to provide for heat resistance during autoclaving. Also in the Nakamura et al patent, a port is affixed to the body of the container after cross-linking has taken place, using non-cross-linked meltable plastic as an adhesive.

Poly(ethylene-vinyl acetate) materials, often referred to as EVA materials, are sufficiently flexible to form containers usable in the medical field. One advantage of EVA materials is that they do not require plasticizers, as do polyvinyl chloride materials. As a result, the quantity of leachable materials or extractable components can be essentially eliminated from the plastic film. Further, prior to cross-linking, the EVA material is easily heat-sealable employing, for example, dielectric heating methods using radio frequency voltages between metal heat sealing discs.

However, known conventional containers made from EVA materials have certain distinct disadvantages. For example, when subjected to pasteurizing or autoclaving temperatures on the order of 110° C. or more, the EVA materials tend to soften, distort or melt. The softening effect can be inhibited by high energy irradiation of the EVA material to provide the necessary and desirable cross-linking, thus improving the heat-resistant characteristics of the EVA material. However, all heat-sealing of the material to provide fluid resistant seals must be performed prior to the irradiation step.

In addition, known conventional EVA containers tend to have wall thicknesses on the order of 0.015 inch. This wall thickness has been conventionally utilized in connection with radio frequency, dielectric heat sealing, because it results in acceptable heat sealed joints with minimal electric arcing, given present techniques and manufacturing equipment. Additionally, such wall thicknesses provide an acceptable level of strength.

However, with conventional single layer EVA films, irradiation doses on the order of 15 to 40 megarads are required to produce the degree of cross-linking necessary to withstand sterilization temperatures. Such high irradiation dosage levels, coupled with the relatively large amounts of EVA materials present, cause undesirably high amounts of acetic acids or other extractable materials. The acetic acid produced is undesirable because it can be absorbed by the contents of the container.

Therefore, when using EVA materials in the medical field, it is desirable to use lower irradiation doses and lesser amounts of EVA materials, thereby producing lesser amounts of acetic acid and other extractable by-products.

Further, known conventional EVA materials suffer from a further disadvantage in that the extrusion process must be carefully designed and controlled. A lack of control during the extrusion process can result in internal stresses, or "frozen-in" stresses, in the material. At room temperature these stresses may be of minimum consequence. However, when containers formed of internally stressed materials are heated within a sterilizing unit, such as a steam autoclave, the internal stresses can lead to excessive shrinkage or distortion of the heated container. In extreme cases, these internal stresses can even cause the containers to rupture.

In addition, known conventional containers formed of EVA materials have to be positioned carefully during sterilization. Adjacent containers in the sterilizing unit tend to adhere or stick to one another due the melting and recrystallizing of the EVA material, even though it may have been sufficiently cross-linked to prevent distortion.

In addition to all of the above-stated disadvantages, containers made of flexible plastics which are radiation crosslinkable, as are EVA materials, are also highly permeable to water, oxygen, and carbon dioxide. Therefore, such containers simply cannot be used for storing aqueous solutions without employing a barrier overwrap. This only adds to the overall expense of the container, while at the same time detracting from user convenience.

One objective of this invention is to provide a medical grade, transparent, flexible plastic container which is readily fillable and drainable, which does not incorporate materials having plasticizers, and which minimizes migration of materials, such as acetic acid, into the contents of the container.

Another objective of this invention is to provide such a container which is as strong as prior art containers, being able to withstand a six foot drop test when filled.

Still another objective of this invention is to provide such a container which will be less subject to distorting or rupturing, due to internal stresses, when heat sterilized and will exhibit little or no container-to-container tackiness during or after heat sterilization.

Yet another objective of this invention is to provide a container which integrally includes barrier materials, eliminating the need for a separate barrier overwrap, thereby adding to the overall economies and the convenience of use.

Still another objective of this invention is to provide a container which, in addition to the above-stated advantages, can be formed using dielectric radio frequency heat sealing methods, thereby providing stronger fluid resistant seals than are possible with impulse or hot-bar heat sealing methods.

SUMMARY OF THE INVENTION

To achieve these and other objectives, the invention provides a sterilizable multi-layer plastic film from which containers can be made. One layer is a material which is free or essentially free of extractable plasticizers and which can be heat sealed and then cross-linked using a selected minimal degree of high energy irradiation so as to provide a desired level of heat resistance during sterilization. A second layer is bonded to the first layer. The second layer is formed of a material having higher melting temperature than the first layer. The second layer is also, when compared to the first layer, essentially non-crosslinkable. The second layer provides enhanced physical stability to the overall film and articles made from the film, both during and after sterilization. The second layer also does not exhibit tackiness during sterilization. Preferably, the second layer also provides a barrier to water vapor to prevent evaporation through the film.

The multi-layer film which embodies the features of the invention can be formed either by coextrusion or by lamination.

In a preferred embodiment, the first layer comprises poly(ethylene vinyl acetate), i.e., EVA. In this arrangement, the second layer preferably comprises a high-density linear polyethylene or copolymers consisting substantially of linear polyethylene.

More particularly, the multi-layer plastic material preferably can be formed of an EVA layer having from 10 to 50 weight percent of vinyl acetate units, most preferable 10–35% by weight. The high-density polyethylene layer may also be formed of substantially ethylene copolymers and their blends with lesser amounts of other materials. In addition, substantially crystalline polyolefin may be used, such as polymers of substantially propylene, 4-methyl pentene-1, butene-1 or the like.

Preferably, the multi-layer material will have a thickness on the order of 0.007 inch thick for the EVA material and 0.003 inch thick for the high-density polyethylene material, resulting in an overall thickness of only 0.010 inch.

A container can be formed by positioning two sheets of the multi-layer film adjacent one another with the EVA layers facing each other. The seams of the container can be sealed by means of radio frequency (RF) energy or conductive welding applied to overlapping regions of EVA material. Radio frequency electrodes can be positioned adjacent to the exterior, high-density, polyethylene layers. The energy induced by the RF field causes the EVA layers in the region between the electrodes to heat, melt and fuse together. The polyethylene layers in the same region do not generate heat as the EVA layers do. Hence, the polyethylene layers stay cooler and resist flowing out from between the electrodes. In addition, the higher melting temperature of the second layer, when compared to the first layer, helps prevent excessive thinning or cut-through by conductive heat sealing elements.

The exterior two layers of polyethylene thus provide physical and structural stability to the seam while the EVA material is in a liquid state and can readily flow. Further, the non-melted polyethylene layers do not flow from between the RF electrodes. This prevents the electrodes from coming too close to each other, with resultant arcing, which results in inadequate and non-uniform seals. As a result of this interaction between the high-density exterior polyethylene layers, a much more consistent heat seal is created.

The inwardly oriented EVA layers, when heat sealed together in the manner just described, form a non-leaking container. In this container, the contents are in contact only with surfaces of the EVA layers, which are free of plasticizers. In this configuration, the higher strength, higher temperature resistant, high-density polyethylene exterior layers, in combination with the cross-linked EVA-layers, provide a container as strong as, but more temperature resistant than containers made using single layer EVA films.

Because the EVA layer in the multi-layer material is relatively thin and supported by the second polyethylene layer, the composite can be cross-linked to the desired degree by exposure to a selected, relatively low, level of irradiation, on the order of 5 to 10 megarads. Because of this lower radiation dosage, fewer extractable by-products, such as acetic acid or the like, are produced by the material during the irradiation step. Subsequently, the container can be filled with a selected fluid or solid and the entire unit can be sterilized without developing leaks.

Sterilization can be by means of an autoclave, as is conventional. Alternately, instead of steam sterilization, dry heat or radiation sterilization may also be used to sterilize both the container and its contents.

When the material is coextruded, any internal stresses that may be present in the EVA layer of the coextruded material will be partly supported by the high-density polyethylene layer during the heat sterilization process. As a result, there is less relaxation, shrinkage or distortion during sterilization.

In accordance with another aspect of the invention, the container includes a port formed of a tubular member of multi-layer material. In this configuration, the EVA layer is positioned on an exterior surface of the port. The high-density polyethylene is positioned on an interior peripheral surface of the port. The port is positioned between unsealed, overlapping regions of the body portion of the container. The exterior EVA layer of the port is thus located adjacent the interior EVA layers of the body section.

The body portions of the container and the adjacent port may be heat sealed together using RF energy. A portion of the exterior EVA layer of the port member will be heat sealed to adjacent regions of EVA material of the body section. The container and port can then be subjected to irradiation, preferably on the order of 7.5 megarads, to produce the desired cross-linking. The EVA layer of the port will be subjected to cross-linking along with the EVA layer of the body portion.

After cross-linking, the container can be filled through the port. The port can then be sealed with a pierceable membrane or the like. The membrane can be formed of high-density polyethylene or other plastics which can withstand the temperatures of sterilization. The membrane can thus be heat sealed to the interior high density polyethylene surface of the port.

Finally, the sealed container and contents can be subjected to sterilization. Sterilization may be achieved using steam sterilization in an autoclave. Dry heat or radiation sterilization may also be used.

In addition to the above-noted benefits, the sealed container of the present invention resists sterilization temperatures in excess of 110° C. without the heat seals failing. Further, the exterior high-density polyethylene surfaces do not exhibit undesirable tacking and do not adhere to adjacent containers while undergoing sterilization.

The container made in accordance with the present invention is especially adapted for storing materials that cannot be irradiated but which can be autoclaved. These include intravenous solutions such as dextrose, lipids, proteins, amino acids, or various drugs.

It will also be understood that materials having more than two layers can also be incorporated into containers in accordance with the present invention.

For example, in yet another aspect of the invention, a three-layer film can be formed. The first and second layers correspond to the EVA and polyethylene layers previously discussed. A third or "skin" layer can be applied over the exposed EVA layer. This skin layer can be a crystalline material such as polyethylene or polypropylene. It can be 0.0001 to 0.001 inch thick with a preferred thickness of 0.0005 inch.

If used in connection with containers of the type previously described, the skin layer is inwardly oriented. The skin layer keeps the EVA surfaces from sticking together during sterilization. Thus, in addition to having non-tacking, exterior polyethylene surfaces, such containers have non-tacking interior surfaces as well.

The three layer film may also be used in containers whose contents might be readily absorbed by exposed surfaces of EVA material. For example, nitroglycerine is readily absorbed by EVA materials. Such a substance could be stored in a container formed of the above-noted three layer film, as the skin layer eliminates such absorption.

In a further aspect of the invention, a multiple layer composite film can also be formed by either incorporating a third layer between the inner layer of EVA material and the outer layer of polyethylene, or by incorporating a third layer within the EVA layer itself. When positioned between the EVA layer and the polyethylene layer, the third layer could be formed of poly(ethylene vinyl alcohol), referred to as EVAL. When positioned within the EVA layer, the third layer could be formed of either EVAL or poly-vinylidine chloride, referred to as PVDC. In either embodiment, the third layer functions as a gas barrier layer. It can have a thickness in a range of 0.0001 to 0.005 inch, preferably in a range of 0.0005 to 0.002 inch.

In still another aspect of the invention, a multiple layer composite film can be formed, adding a polyethylene skin layer (as previously described) to the EVA-EVAL/PVDC-polyethylene composite as just discussed.

Containers formed of the above-noted multiple layer composite films can be readily heat sealed as discussed above. While the skin layer does not generate heat in the applied RF electric field, at the above-noted thicknesses it will absorb the heat from the adjacent EVA layer and melt to contribute to the formation of a suitable heat seal.

Numerous other advantages and features of the present invention will become readily apparent from the following detailed description of the invention and the embodiments thereof, from the claims and from the accompanying drawings in which the details of the invention are fully and completely disclosed as a part of this specification.

DESCRIPTION OF THE DRAWINGS

FIG. 1 is a view in perspective of a two layer section of the multi-layer film material which embodies the features of the invention;

FIG. 2 is a sectional view of a portion of the multi-layer film of FIG. 1;

FIG. 3 illustrates a first step in forming a pouch of multi-layer film in accordance with the present invention;

FIG. 4 illustrates schematically heat sealing regions of the pouch of multi-layer film of FIG. 3;

FIG. 5 is an end view, partly broken away, of the pouch of FIG. 4;

FIG. 10 is an enlarged view, in section, of an alternate port usable in accordance with the present invention; and.

FIG. 11 is a sectional view of one embodiment of a three layer film material which embodies the features of the invention;

FIG. 12 is a perspective view of the orientation of two sheets of the three layer films shown in FIG. 11 in the formation of the container;

FIG. 13 is a sectional view of another embodiment of a four layer film material which embodies the features of the invention;

FIG. 14 is a sectional view of a three layer film material which embodies the features of the invention;

FIG. 15 is a sectional view of a multiple layer composite film material which embodies the features of the invention; and FIG. 16 is a sectional view of another multiple layer composite film material which embodies the features of the invention.

Figure 6:
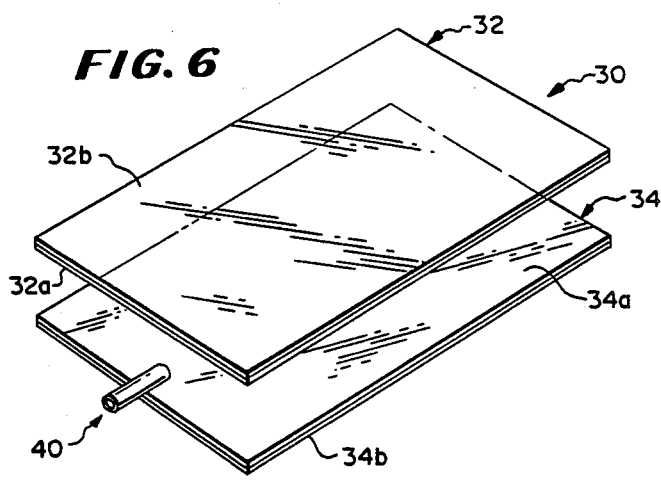
FIG. 6 illustrates an initial step in forming a sealed container of multi-layer film in accordance with the present invention.

Before explaining the embodiments of the invention in detail, it is to be understood that the invention is not limited in its application to the details of construction and the arrangement of components as set forth in the following description or as illustrated in the accompanying drawings. The invention is capable of other embodiments and of being practiced or carried out in various ways. Furthermore, it is to be understood that the phraseology and terminology employed herein is for the purpose of description and should not be regarded as limiting.

DESCRIPTION OF THE PREFERRED EMBODIMENTS

With respect to the FIGS., FIG. 1 illustrates a section of multi-layer film 10 having a first layer 12 and a second layer 14. The first layer 12 is composed of a crosslinkable material which is essentially free of leachable, or extractable, plasticizers. In the preferred and illustrated embodiment, the first layer 12 is poly(ethylene-vinyl acetate), referred to as EVA. The EVA layer 12 can be of material having 10 to 50 weight percent of vinyl acetate units and most preferably in a range of 10–35 weight percent, such as 18 weight percent of vinyl acetate units.

The second layer 14 is composed of a material which is, when compared to the material of the first layer 12, essentially non-crosslinkable. In addition, the material of the second layer 14 has a higher melting temperature than the material of the first layer 12. In the preferred and illustrated embodiment, the second layer 14 is high-density polyethylene. The polyethylene layer 14 can have a density of 0.94 to 0.965 g/cm$^3$. Preferably, this density will be in a range of 0.95 to 0.955 g/cm$^3$. The polyethylene layer 14 may include minor amounts of toughening and clarifying agents, such as rubbers and crystal-nucleating compounds.

FIG. 2 is a view in section of the film 10 illustrating the layer 12 bonded to the layer 14.

The EVA layer 12 can be formed with a thickness in a range of 0.005–0.010 inch. The EVA layer 12 begins to soften at temperatures of approximately 60° C., and its crystalline portions begin to melt at temperatures of approximately 85° C.

The second layer 14 of high-density polyethylene can be formed with a thickness in a range of 0.002–0.005 inch. The polyethylene layer 14 begins to soften at temperatures of approximately 125° C., and its crystalline portions begin to melt at temperatures in the range of approximately 135° C. to 140° C. Preferably, the EVA layer 12 has a thickness substantially on the order of 0.007 inch and the high-density, polyethylene layer 14 has a thickness on the order 0.003 inch. The resultant multi-layer material 10, then, has a preferred total thickness on the order of only 0.010 inch.

The multi-layer material 10 can be formed using conventional coextrusion processes which are well-known in the art. It will be understood that alternate forms of bonding, such as those achieved by lamination, could also be used without departing from the spirit and scope of the present invention.

Multi-layer sheet materials, such as the film 10, exhibit desirable heat sealing characteristics and also exhibit low water vapor transmission characteristics. The fact that the material 10 has a thickness of only 0.010 inch, as opposed to a thickness on the order of 0.015 inch as has often been used in the prior art, is also desirable because less material is needed, thereby costing less as well as having lesser amounts of leachable by-products, contaminants, or additives.

The film 10 can then be assembled into a pouch or sealed container utilizing conventional conductive or radio frequency sealing machinery and techniques. Using the film 10, the layer 12, which contains no plasticizers, is the only material in the pouch or container in contact with the contents.

FIG. 3 illustrates a first step in forming a fluid retaining pouch 18 utilizing the film 10. As illustrated in FIG. 3, sheets 20 and 22 of film 10 are positioned adjacent one another, with EVA layers 20a and 22a, respectively, of each of the sheets 20 and 22, inwardly oriented. Layers 20b and 22b, corresponding to the high-density polyethylene layer 14, are outwardly oriented.

The sheets 20 and 22 may then be heat sealed together using RF energy, as illustrated schematically in FIG. 4. In the heat sealing process, a plurality of overlapping, adjacent regions, such as the regions 26, of the EVA layers 20a and 22a are subjected to radio frequency energy as is well-known in the art. As a result, the adjacent EVA material positioned between the electrodes, such as the partial electrode E shown schematically in FIG. 4, melts and fuses together forming a fluid retaining heat seal. The heat seal is indicated by solid lines 28.

A region 28a is not heat sealed together, thereby providing an opening through which the desired contents of the pouch 18 can be later introduced.

It will be understood that the heat seal 28 could be formed in one step with appropriately shaped electrodes. The particular electrodes or other equipment used to form the heat seals are not a limitation of the present invention.

The exterior high-density polyethylene layers, corresponding to the layers 20b and 22b, when positioned between the partial electrodes E, provide physical stability to the heated and molten EVA material during this process. Flow of the material away from the region of the partial electrodes E is minimized because the polyethylene layers resist flowing more than the EVA layers. As a result, much more consistent heat seals are achieved. In addition, the high-density polyethylene layer 14 tends to help reduce electrical arcing problems.

It should be noted that the heat seal 28, as illustrated in FIG. 5, is formed between the molten EVA layers, such as the layers 20a and 22a. In the region of the heat seal 28, the EVA layers 20a and 22a have been fused into a single layer. The exterior layers 20b and 22b continue to retain their separate identity.

The pouch 18 can be irradiated, prior to being filled, with a dose on the order of 5 to 10 megarads, so as to produce the desired cross-linking in the fused EVA layers 20a and 22a and in the heat seal 28. The preferred dose of irradiation is on the order of 7.5 megarads.

It has been found that the pouch 18 as described, when subjected to the above-noted doses of irradiation, exhibits essentially the same impact resistance when dropped and the same heat resistance when sterilized as do bags which are formed with single layer EVA materials on the order of 0.015 inch thick. Such bags, as is well-known, require doses of irradiation on the order of 15 to 40 megarads to produce the desired cross-linking to withstand sterilization temperatures.

The higher doses of irradiation associated with conventional single layer EVA films result in a higher level of acetic acid and other extractables being formed during the manufacturing process. These materials are undesirable because they may contaminate the contents of the pouch 18.

The pouch 18 of FIGS. 4 and 5 can be subsequently filled through the open region 28a with an autoclavable substance, which is designated F in FIG. 5. After it has been filled, the open region 28a of the pouch 18 can be closed by a mechanical clip 27 or the like. The filled pouch 18 can now be sterilized in a steam autoclave. Alternately, dry heat sterilization can be used.

FIG. 6 illustrates an initial step in the formation of a sealed container 30 formed of the multi-layer film 10. The container 30 includes first and second body members 32 and 34. The members 32 and 34 each have inwardly oriented surfaces 32a and 34a, corresponding to the EVA layer 12 of the film 10.

Figure 7:
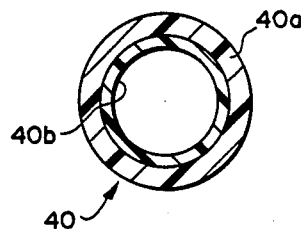
FIG. 7 is an end view of a tubular port usable with the container of FIG. 6.

The container 30 includes a port 40 formed from a coextruded, tubular member formed of the same material as the members 32 and 34. As shown in FIG. 7, the port 40 has an outer EVA layer 40a and an inner, high-density polyethylene layer 40b. The EVA layer 40a forms an exterior surface and the high-density polyethylene layer 40b, forms an interior surface. The port 40 can be positioned between the sheet members 32 and 34 as shown in FIG. 6. When such positioning occurs, the exterior EVA layer 40a is positioned adjacent the interior EVA layers 32a and 34a of the members 32 and 34.

Alternately (not shown), the port 40 may comprise a single EVA layer or multiple layers of various other materials with an outer layer of EVA and, optionally, an inner layer of EVA as well.

Figure 8:
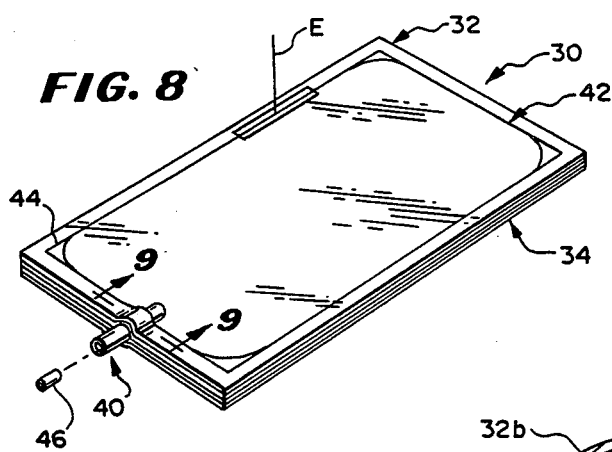
FIG. 8 illustrates schematically heat sealing regions of the container of FIG. 6.

As illustrated in FIG. 8, partial electrodes E, illustrated in schematic form, can be used to apply radio frequency energy to the overlapping regions 42 of the members 32 and 34. This RF heats and fuses the EVA layers 32a and 34a thereby creating a contents-retaining heat seal 44 indicated in solid lines.

Figure 9:
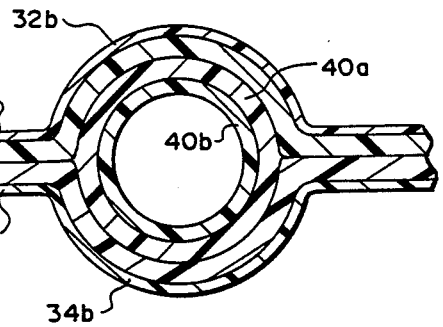
FIG. 9 is a view in section, taken along line 9—9 of FIG. 8 illustrating the heat seal between the port and the body portion of the container.

In addition, as illustrated in FIG. 9, electrodes E can be used to apply radio frequency energy to the region of the port 40 so as to bond the EVA layer 40a to the adjacent regions of the EVA layers 32a and 34a of the members 32 and 34. Hence, the container 30 as illustrated in FIG. 8 includes the integrally bonded port 40 as well as a sealed body portion formed of the members 32 and 34.

Subsequently, the container 30 can be subjected to irradiation, on the order of 7.5 megarads and then can be filled with an autoclavable substance. A seal means 46 such as a high-density polyethylene membrane can be inserted into the port 40 in contact with the interior surface 40b. The seal means 46 can then be heat sealed to the high density, polyethylene member 40b closing the port 38. Alternately, the seal means 46 may be butt-welded to the port 38 by a hot-platen method.

The sealed and filled container can now be sterilized using steam sterilization. Alternately, dry heat sterilization can be used.

As a result of the cross-linking operation to which the members 32, 34 and the port 40 have been subjected, in combination with the high-density, polyethylene layer, the container 30 will be stable at temperatures on the order of 110°–121° C. or more during the sterilization process. Additionally, due to the exterior polyethylene layer, such as the layer 14 of the film 10, the container 30 will not become tacky and will not adhere to adjacent containers while being sterilized.

A further advantage of the container 30 is found in the fact that the additional structural integrity imparted to the container by the high-density, polyethylene layer minimizes shrinkage or distortion during the sterilization process due to internal stresses that might be formed in the EVA layer during the extrusion process. Additionally, the container 30 exhibits improved lower water vapor transmission characteristics and does not require an overpouch to avoid loss of water from aqueous contents during storage.

Figure 10:
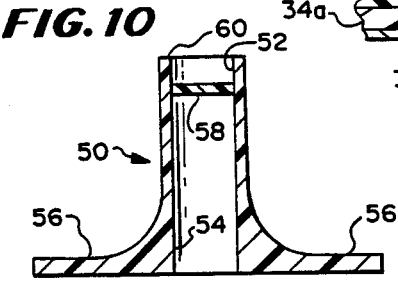

FIG. 10 illustrates in section an alternate port 50. The port 50 is cylindrical with a bore 52 defined therein. At a lower end 54, an integrally formed mounting flange 56 is formed.

The port 50 is formed of mono-layer high density polyethylene. It thus may be affixed to the outer surface 20b of the pouch 18 or the outer surface 32b of the container 30 by heat sealing of the flange 56. The port 50 could be heat sealed to the bag 18 or container 30 at any convenient location.

The port 50 could be used both for filling or draining the pouch 18 or container 30. A sealing membrane 58 can be heat sealed to an upper end 60 of the port 50 or anywhere within the bore of the port.

The port 50, having an interior surface of polyethylene, has a coefficient of friction which is less than the coefficient of friction of EVA. Thus, the port 50 may be more easily penetrated by an inserted cannula than the port 40, having an interior EVA surface. However, the port 40, having a higher coefficient of friction, serves to prevent the inadvertant removal of the cannula. Of course, the choice of materials depends upon the particular article of manufacture and the medical contents.

A multiple, three-layer composite film 62 which embodies the features of the invention is shown in FIGS. 11 and 12. The first and second layers 64 and 66 correspond, respectively, to the EVA and polyethylene layers previously discussed.

In FIG. 11, a third or "skin layer" 68 is applied over the exposed EVA layer 64. This skin layer 68 can be a crystalline material such as polyethylene, polypropylene, or copolymers, blends, and alloys thereof. It can be 0.0001 to 0.001 inch thick, with a preferred thickness of 0.0005 inch.

If used to form a fluid retaining pouch or container of the types previously described, the skin layer 68 is inwardly oriented, as shown in FIG. 12. The multiple layer composite film 62 is especially useful in certain applications. In blood processing, for example, transfer sets are often formed with multiple, sterile, empty containers. The skin layer 68 keeps the EVA surfaces 64 from sticking together during sterilization. Thus, in addition to having non-tacking polyethylene exterior surfaces 66, such containers have non-tacking interior surfaces 68 as well.

Another application of the above-noted multiple layer composite film 62 is in containers whose contents might be readily absorbed by exposed surfaces of EVA material. For example, nitroglycerine is readily absorbed by EVA materials. However, such a substance could be stored in a container formed of a above-noted multiple layer composite film 62, as the skin layer 68 eliminates such absorption.

A multiple, four-layer composite film 63 which embodies the features of the invention is shown in FIG. 13. There, a fourth layer 70 is incorporated in the film between the layer of EVA material 64 and the thicker of the two layers of polyethylene, i.e. layer 66. The fourth layer 70 could be formed of poly(ethylene-vinyl alcohol), referred to as EVAL. This fourth layer 70 functions as a gas and vapor barrier layer. It can have a thickness in a range of 0.0001 to 0.005 inch, preferably in a range of 0.005 to 0.002 inch. In four layer films, both the skin layer 68 and the fourth layer 70 add further mechanical and thermal support to the EVA layer 64.

As shown in FIG. 14, the gas and vapor barrier layer 70 can be used in a three layer film 65 as well, positioned inbetween the EVA layer 64 and the polyethylene layer 66.

Another multiple layer composite film 67 which embodies the features of the invention is shown in FIG. 15. Here, the layer 70 is positioned within the EVA layer 64. In this arrangement, the layer 70 can be formed either of EVAL; poly(ethylene-vinyl alcohol); or poly (vinylidine chloride), referred to as PVDC. This layer 70 serves as a water and gas vapor barrier, as in the FIGS. 13 and 14 embodiments.

As shown in FIG. 15, the composite film 67 can also include, in addition to the polyethylene layer 66, the skin layer 68 for the same purposes described with respect to the FIGS. 11 to 13 embodiments. Alternately, as shown in FIG. 16, a composite film 69 can include the layer 70 positioned within the EVA layer 64 in conjunction with only the polyethylene layer 66.

The composite films 62, 63, 65, 67, and 69 can be formed by either lamination or coextrusion.

Containers formed of the above-noted multiple layer composite films can be readily heat sealed as discussed above. While the skin layer 68, if present, does not generate heat in the applied RF electrical field, at the above-noted thicknesses, it will absorb enough heat from the adjacent EVA layer and melt to form a suitable heat seal.

From the foregoing, it will be observed that numerous variations and modifications may be effected without departing from the true spirit and scope of the novel concept of the invention. It is to be understood that no limitations with respect to the specific apparatus illustrated herein is intended or should be inferred. It is, of course, intended to cover by the appended claims all such modifications as fall within the scope of the claims.

I claim:

1. A method of fabricating a heat sterilizable stress-free container comprising the steps of:

forming first and second film members, each having at least two integral layers, the first of the layers formed of a material which is cross-linkable and free or essentially free of leachable plasticizers and which has a heat distortion temperature at or below 110° C., the first layer material being selectively cross-linkable to obtain the desired resistance to distortion at heat sterilization temperatures, the second of the layers formed of a material which, when compared to the first layer material, is not cross-linkable and which has a heat distortion temperature above 110° C.;

positioning the first and second film members in overlapping relationship with corresponding first layers of each adjacent one another so as to form inner surfaces of the container;

melting a peripheral region of the overlapping, adjacent first layers of the container using heat sealing elements without pre-stressing said film members to form a peripheral seal between the inner first layers of the container;

irradiating the container so as to cross-link the first layers to obtain the desired resistance to melting; and sterilizing the container by exposure to heat at or above 110° C. without pre-stressing the material, to form a non-stressed, non-heat shrinkable container.

2. A method as in claim 1 wherein, during said irradiation step, the dosage of irradiation is in a range of 5–10 megarads.

3. A method as in claim 2 wherein the dosage of irradiation corresponds substantially to 7.5 megarads.

4. A method as in claim 1 and further including the step of affixing a port to a selected region of at least one film member.

5. A method as in claim 4 wherein said port affixing step includes heat sealing the port to the film member.

6. A method as in claim 4 further including the step of forming the port with an outer cylindrical surface of cross-linkable material;

and wherein said port affixing step includes positioning the outer peripheral, cylindrical surface of the port between regions of the inner first layers of the container so that, during said melting step, regions of the outer peripheral cylindrical surface of the port and the adjacent regions of the inner first layers melt together to form a substance retaining seal therebetween.

7. A method as in claim 1, wherein in said step of forming the first and second film members, at least one of the film members is formed by coextrusion.

8. A method as in claim 1 wherein in said step of forming the first and second film members, at least one of the film members is formed by lamination.

9. The method of claim 1 wherein said step of melting said peripheral region includes melting said region by radio frequency dielectric heating and wherein said second layer stays cooler to prevent thinning or cut-through by the heat sealing elements.

* * * * *